United States Patent [19]

Black

[11] Patent Number: 5,188,827
[45] Date of Patent: Feb. 23, 1993

[54] USE OF INTERLEUKIN-4- FOR LOWERING BLOOD-CHOLESTEROL LEVELS

[75] Inventor: Hugh E. Black, Sparta, N.J.

[73] Assignee: Schering Corporation, Kenilworth, N.J.

[21] Appl. No.: 688,615

[22] PCT Filed: Dec. 18, 1989

[86] PCT No.: PCT/US89/05532
§ 371 Date: Jun. 10, 1991
§ 102(e) Date: Jun. 10, 1991

[51] Int. Cl.$^5$ ............................................. A61K 45/05
[52] U.S. Cl. ................................... 424/85.2; 424/85.1
[58] Field of Search ............................. 424/85.2, 85.1

[56] References Cited

FOREIGN PATENT DOCUMENTS 0230107 7/1987 European Pat. Off. .

OTHER PUBLICATIONS

Nimer et al., JAMA, 1988, vol. 260(22) pp. 3297–3300.
Malmendier et al. Atherosclerosis 73: 173–180 (1988).

Primary Examiner—Lester L. Lee
Assistant Examiner—Choon Koh
Attorney, Agent, or Firm—Paul Lunn; Norman Dulak; James Nelson

[57] ABSTRACT

A method for lowering the blood-serum cholesterol levels in mammals by administering IL–4 is disclosed as well as the use of IL–4 for the manufacture of a medicament for use in lowering blood-serum cholesterol levels.

10 Claims, 4 Drawing Sheets

USE OF INTERLEUKIN-4- FOR LOWERING BLOOD-CHOLESTEROL LEVELS

BACKGROUND OF THE INVENTION

This invention relates to the lowering of blood cholesterol levels in mammals by administering a cholesterol lowering effective amount of interleukin-4 (IL-4).

Interleukin-4 (IL-4) is a lymphokine (stimulator of the immune system) that has a broad range of immune cell stimulation as described in Banchereau et al., *Lymphokine Res.* Vol. 6, No. 1: U135 (1987); Yokoto et al., *Proc. Natl. Acad. Sci. USA*, 83: 5894-5898 (1986); Lee at al., *Proc. Natl. Acad. Sci. USA*, 83: 2061-2065 (1986); Coffman et al., *J. Immunol.* 136: 949-954 (1986); Sanderson et al., *Proc. Natl. Acad. Sci. USA*, 83: 437-440 (1986); Grabstein et al., *J. Exp. Med.*, 163: 1405-1413 (1985); and Vitetta et al., *J. Exp. Med.* 162: 1726-1731 (1985). During its early development IL-4 has also been referred to as B-cell growth factor (BCGF) [Butler et al., *J. Immunol.* 133: 251-255 (1984)(human BCGF); and Farrar et al., *J. Immunol.* 131: 1838-1842 (1983)(mouse BCGF)] and B-cell stimulatory factor 1 (BSF-1) [Ohara et al., *J. Immunol.* 135: 2518-2523 (1985)]. The clarification and designation of the name interleukin-4 was finally proposed and adopted in 1986 [Sanderson et al., *Proc. Natl. Acad. Sci. USA*, 83: 437-440 (1986)].

SUMMARY OF THE INVENTION

The method of this invention involves administering to mammals a serum cholesterol lowering effective amount of IL-4. Preferably, the IL-4 is administered to mammals diagnosed as having elevated blood serum cholesterol levels (hypercholesterolemia). The invention also relates to the use of IL-4 for the manufacture of a medicament for lowering blood serum cholesterol levels.

Preferably, the IL-4 employed is derived from a human source. Preferably the dosage form is one suitable for administration by intravenous injection or intravenous infusion and administration will suitably be in an amount of about 0.5 to about 600 micrograms of IL-4 per kilogram of body weight per day. Preferably, the IL-4 is administered in an amount of about 0.5 to about 125 micrograms of IL-4 per kilogram of body weight per day, and most preferably about 0.5 to about 30 micrograms of IL-4 per kilogram of body weight per day.

DETAILED DESCRIPTION OF THE INVENTION

Figure 1A:
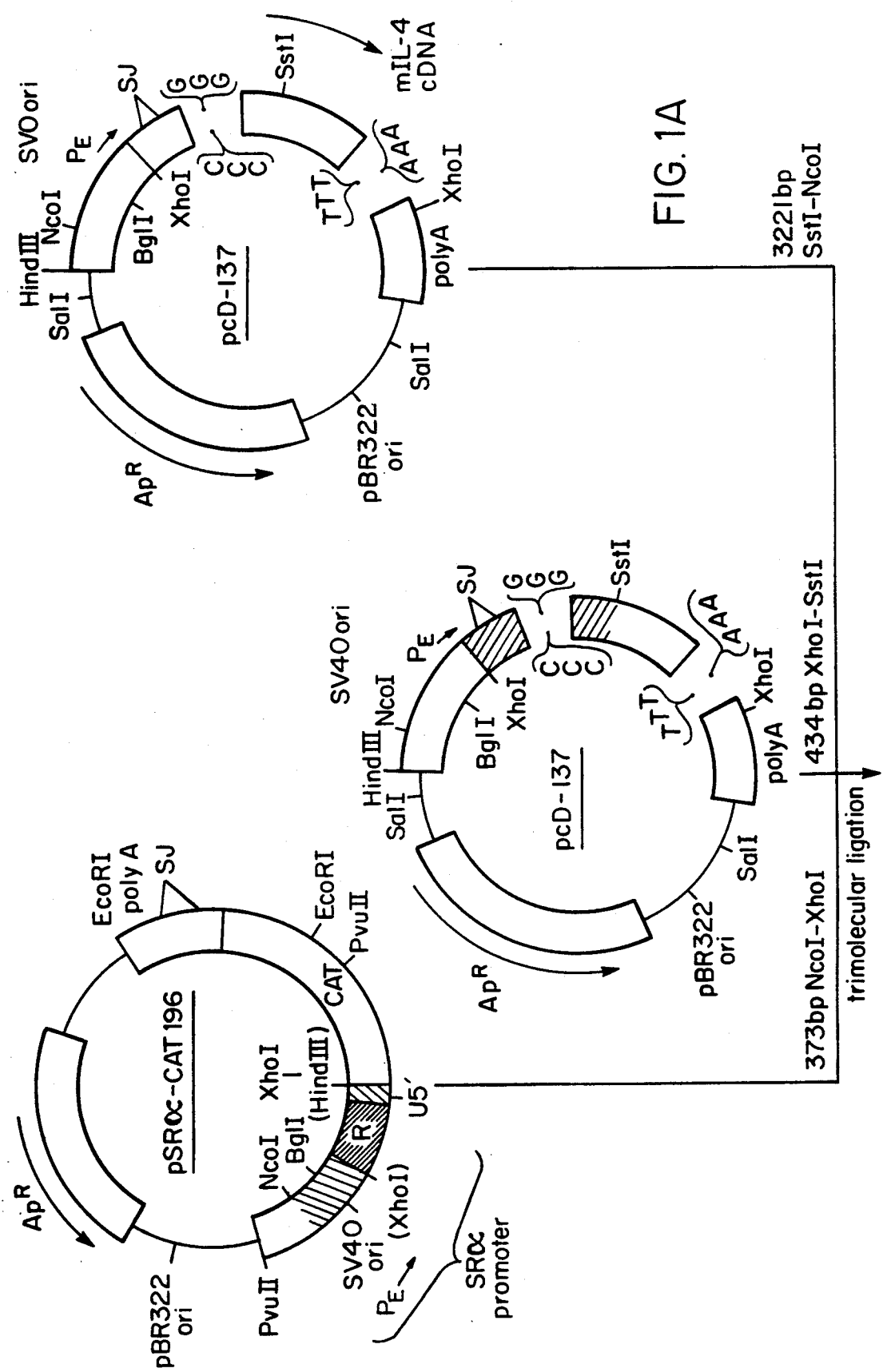
FIGS. 1a-d illustrate a construction map for the expression of human IL-4 in the vector pdhfr-SRalpha263.

The invention provides a method for lowering blood cholesterol levels in mammals, e.g., mammals with hypercholesterolemia, by administering to said mammals a serum cholesterol lowering effective amount of IL-4. The invention also provides for the use of IL-4 for the manufacture of a medicament for lowering blood serum cholesterol levels.

Any suitable IL-4 may be employed in the present invention. Complementary DNAs (cDNAs) for IL-4 have recently been cloned and sequenced by a number of laboratories, e.g. Yokoto et al., *Proc. Natl. Acad. Sci. USA*, 83: 5894-5898 (1986) (human); Lee at al., *Proc. Natl. Acad. Sci. USA*, 83: 2061-2065 (1986)(mouse); Noma et al., *Nature* 319: 640-646 (1986)(mouse); and Genzyme Corporation, Boston, Mass. (human and mouse). Moreover, non-recombinant IL-4 has been purified from various culture supernatants, e.g. Sanderson et al., *Proc. Natl. Acad. Sci. USA*, 83: 437-440 (1986)(mouse); Grabstein et al., *J. Exp. Med.*, 163: 1405-1413 (1985)(mouse); Ohara et al., *J. Immunol.*, 135: 2518-2523 (1985)(mouse BSF-1); Butler et al., *J. Immunol.*, 133: 251-255 (1984)(human BCGF); and Farrar et al., *J. Immunol.*, 131: 1838-1842 (1983)(mouse BCGF). The disclosures of all the above articles are incorporated herein by reference for their teachings of DNA and amino acid sequences and of methods of obtaining suitable IL-4 materials for use in the present invention.

Preferably, the IL-4 used in the present invention will be a human IL-4, and most preferably it will be the human version with the sequence described in Yokoto et al., *Proc. Natl. Acad. Sci. USA*, 83: 5894-5898 (1986) and PCT Patent Application No. 87/02990 published May 21, 1987 that is expressed in and isolated from *E. coli* (U.S. patent application Ser. No. 079,666, filed Jul. 29, 1987 and U.S. patent application Ser. No. 194,799, filed Jul. 12, 1988). The disclosures of the above articles, PCT Application and U.S. Patent Application are hereby incorporated herein by reference.

According to this invention, mammals are administered a serum cholesterol lowering effective amount of an IL-4. A serum cholesterol lowering effective amount is defined as any amount that will significantly lower the cholesterol level, with a lowering of cholesterol by at least 5 percent considered significant. From about 0.5 to about 600 micrograms of IL-4, preferably human IL-4 (hIL-4), per kilogram of body weight per day is preferably administered. More preferably, mammals are administered about 0.5 to about 125 micrograms of hIL-4 per kilogram of body weight per day, and most preferably mammals are administered about 0.5 to about 30 micrograms of hIL-4 per kilogram of body weight per day.

The amount, frequency and period of administration will vary depending upon factors such as the cholesterol level (e.g., the severity of the cholesterol elevation), age of the patient, nutrition, etc. Usually, the administration will be daily initially and it may continue periodically during the patient's lifetime. Dosage amount and frequency may be determined during initial screenings of cholesterol levels and the magnitude of the effect of IL-4 upon the lowering of the cholesterol levels. Dosage will be aimed to lower the cholesterol level to an acceptable level of about 240 milligrams of cholesterol per deciliter of blood serum, preferably about 200 milligrams of cholesterol per deciliter of blood serum.

To complement the cholesterol lowering effect of the IL-4, it may be useful to administer it in conjunction with other pharmaceutically active compounds. For example, it can be combined with other cholesterol lowering agents [e.g., granulocyte-macrophage colony stimulating factor (GM-CSF)(U.S. Patent Application of Melvin D. Brannan and Hugh E. Black of Perkasie, Pa. and Sparta, N.J., respectively, entitled "METHOD FOR LOWERING BLOOD CHOLESTEROL LEVELS WITH GRANULOCYTE-MACROPHAGE COLONY STIMULATING FACTOR" filed on or about Dec. 16, 1988); lovastatin (1,2,3,7,8,8a-hexahydro-3,7-dimethyl-8-[2-(tetrahydro-4-hydroxy-6-oxo-2H-pyran-2-yl)-ethyl]-1-naphthalenyl 2-methylbutanoate, (U.S. Pat. No. 4,231,938)) available from Merck, Inc., Rahway, N.J.; gemfribrozil (5-(2,5-dimethylphenoxy)-2,2-dimethylpentanoic acid), available from Parke-Davis, Inc., Ann Arbor, Mich.; dilevalol (5-{1-hydroxy-2-[(1-methyl-3-phenylpropyl)amino]ethyl} salicylamide (U.S. Pat. No. 4,788,183)); and pravastatin, which is available from Squibb, Inc., Princeton, N.J.]. For lowering cholesterol levels that may be associated with acute manifestations of heart disease such as myocardial infarction, IL-4 can be administered in conjunction with thrombolytic agents [e.g., tissue plasminogen activators (tPAs) (for example, those disclosed in U.S. Pat. Nos. 4,370,417, 4,752,603; U.K. Patent No. 2,119.804; PCT Patent Application Nos. 87/05934, 87/04722, 84/01786; Australian Patent Application No. 55514/86; EPO Patent Application Nos. 227,462, 234,051, 238,304, and 174,835, and the tPA that is commercially available from Genentech, Inc., South San Francisco, Calif.); eminase (available from Beecham Inc., Bristol, Tenn., and Upjohn Corporation, Kalamazoo, Mich.); and streptokinase (for example, the materials disclosed in European Patent Application Nos. 248,227, 28,489; and the streptokinase commercially available from Burroughs-Wellcome, Inc., Research Triangle, N.C.)] or combinations of such thrombolytic agents (for example, see European Patent Application Nos. 91,240 and 28,489 for streptokinase/tPA complexes). These references are hereby incorporated by reference to illustrate examples of other cholesterol lowering agents and thrombolytic agents that can be used in combination with IL-4 in certain embodiments of the present invention. The specific cholesterol lowering agents and thrombolytic agents mentioned above are merely examples of such agents known to those skilled in the art that can be used in the practice of the present invention.

Administration of the dose can be intravenous, nasal, parenteral, oral, subcutaneous, intramuscular, topical, transdermal or any other acceptable method. The IL-4 could be administered in any number of conventional dosage forms. Parenteral preparations include sterile of conventional dosage forms. Parenteral preparations include sterile solutions or suspensions. Inhalation administration can be in the form of a nasal or oral spray, or by insufflation. Topical dosage forms can be creams, ointments, lotions, transdermal devices (e.g., of the conventional resevoir or matrix patch type) and the like.

The formulations and pharmaceutical compositions contemplated by the above dosage forms can be prepared with conventional pharmaceutically acceptable excipients and additives, using conventional techniques.

Presently, the IL-4 is administered via the intravenous route. The solutions to be administered may be reconstituted lypholized powders and they may additionally contain preservatives, buffers, dispersants, etc. Preferably, IL-4 is reconstituted with 10 millimolar citrate buffer and preservative-free sterile water with the maximum concentration not to exceed 1500 micrograms per milliliter and administered by continuous intravenous infusion or by intravenous injection. For continuous infusion, the daily dose can be added to 5 ml of normal saline and the solution infused by mechanical pump or by gravity.

The effect of IL-4 on lowering the serum cholesterol levels in mammals was determined by the following test protocol.

Cynomolgus monkeys (Macaca fascicularis) are administered human IL-4, which is obtained from Chinese Hamster Ovary (CHO) cells as described below. The route of administering the human IL-4 is by intravenous injection in the saphenous vein for about 15 seconds and dosing occurs daily for four weeks. Blood samples are taken at the times indicated in the following table by femoral venipuncture following an overnight fast. Blood samples are taken at two times prior to dosing with the human IL-4 (−2 and −1 weeks prior to initial Il-4 dosing) and control animals (receiving IL-4 doses of 0.0 mg/kg/day in Table 1) are maintained that never received any dose of the human IL-4. The blood samples are checked for blood cholesterol levels using an enzymatic DACOS analyzer which is commercially available from Coulter Electronics, Inc., 600 West 20 Street, Hialeah, Fla. 33010.

Taking the averages for the various doses in Table 1 resulted in percent lowering of cholesterol levels of 9% (after 3 weeks) and 7% (after 4 weeks) at 0.025 mg/kg dose, 30% (after 3 weeks) and 20% (after 4 weeks) at 0.125 mg/kg dose, and 49% (after 2 weeks) at 0.600 mg/kg dose Construction of the Human IL-4 Expression Plasmid pdhfr-SRalpha263

Figure 1B:
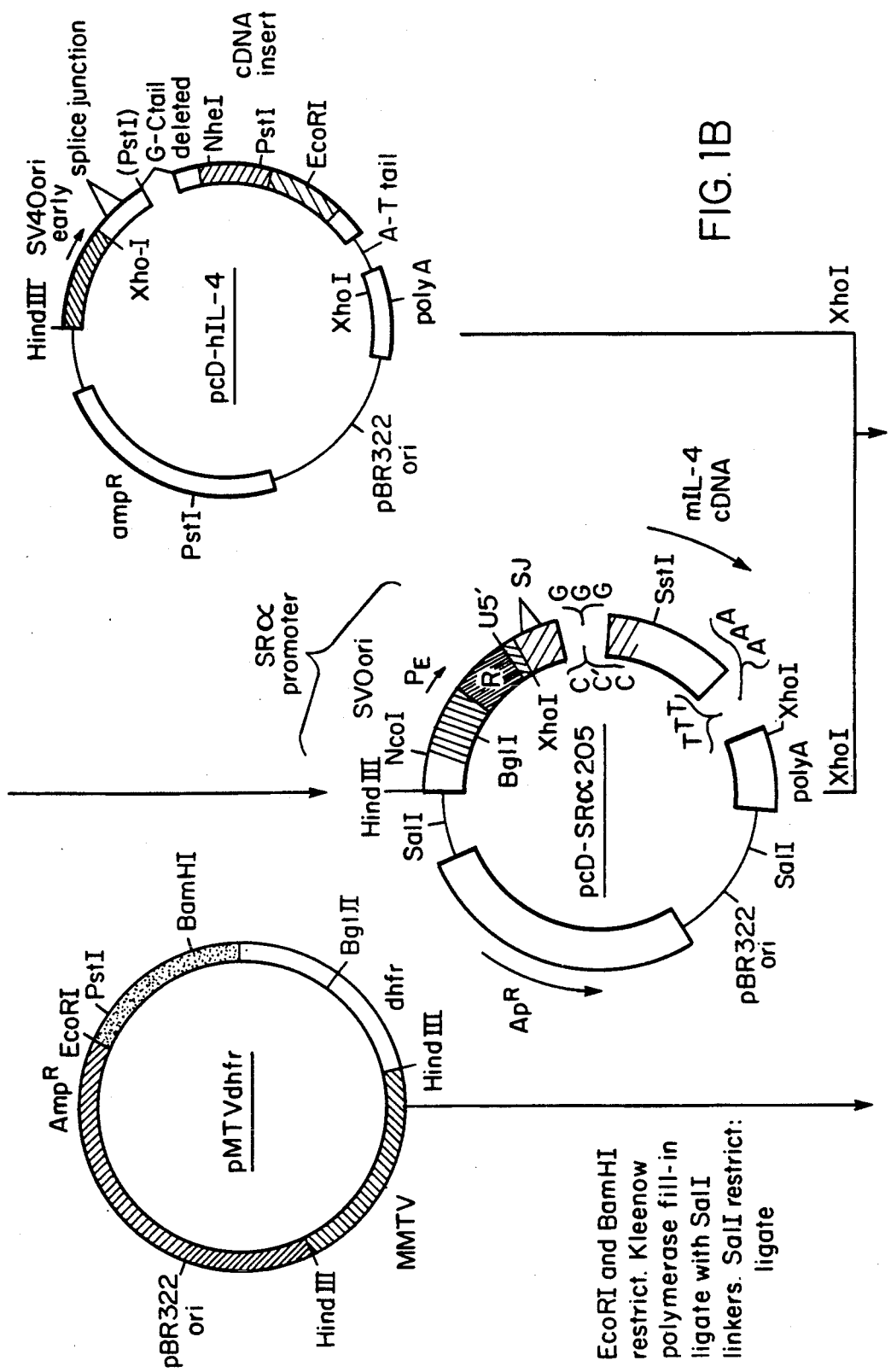

The construction of plasmids pSRa-CAT196, pcD137, pcD-SRa205, pcDhIL-4 clone 125 and pcD-SRa224 have been described (Takebe et al., *Molecular and Cellular Biology*, 8: 466–477 (1988); and Yokoto et al., *Proc. Natl. Acad. Sci. USA*, 83: 5894–5898 (1986)). As shown in FIG. 1a, plasmid pcD-SRa-205 was constructed by the trimolecular ligation of the 373 bp NcoI-XhoI SRa promoter fragment from pSRa-CAT196, the 434 bp XhoI-SstI splice junction (SJ) and 5′ murine IL-4 (mIL-4) fragment from pcD137 and the 3221 bp SstI-NcoI fragment, also from pcD137, containing the 3′ murine IL-4 cDNA, SV40 polyadenylation region and the pBR322 derived plasmid backbone containing the origin of replication and ampicillin resistance gene. The G-C tail was deleted from pcD-hIL-4 clone 46 (Yokoto et al., *Proc. Natl. Acad. Sci. USA*, 83: 5894–5898)) as follows. The Okayama-Berg plasmid pL1 (Okayma and Berg, *Molecular and Cellular Biology*, 3: 280–289 (1983)) was restricted with PstI and the four nucleotide overhang removed by the 3′-5′ exonuclease activity of T4 polymerase. BglII linkers were ligated to the flush DNA ends followed by restriction with BglII and HindIII. The HindIII BglII fragment containing the SV40 sequence of was isolated and inserted into BglII/HindIII restricted pcD-MCGF (Yokoto et al., *Proc. Natl. Acad. Sci. USA*, 81: 1070–1074 (1984)) to yield intermediate plasmid 101. The purified 3IIbp Pst fragment from plasmid pcD-hIL-4 clone 46 was restricted with Sau3A-I which releases a 163bp fragment with overhangs compatible with BglII. The 162bp fragment was ligated to BglII restricted p101 to yield intermediate 112. The HindIII/NheI fragement to p112 containing SV40 and human IL-4 cDNA sequences was ligated to HindIII/NheI restricted clone 46 DNA to produce pcD-hIL-4 clone 125 containing an SV40 early promoter, SV40 splice junction and complete human IL-4 cDNA with the G-C tail deleted. As shown in FIG. 1b plasmid pcD-Sra224 was constructed by replacing the small XhoI fragment of pcD-SRa205 (containing the SJ and mIL4 cDNA) with the small XhoI fragment of pcDhIL-4 clone 125 containing the SJ and HIL-4 cDNA with G-C tail deleted as described above.

Figure 1C:
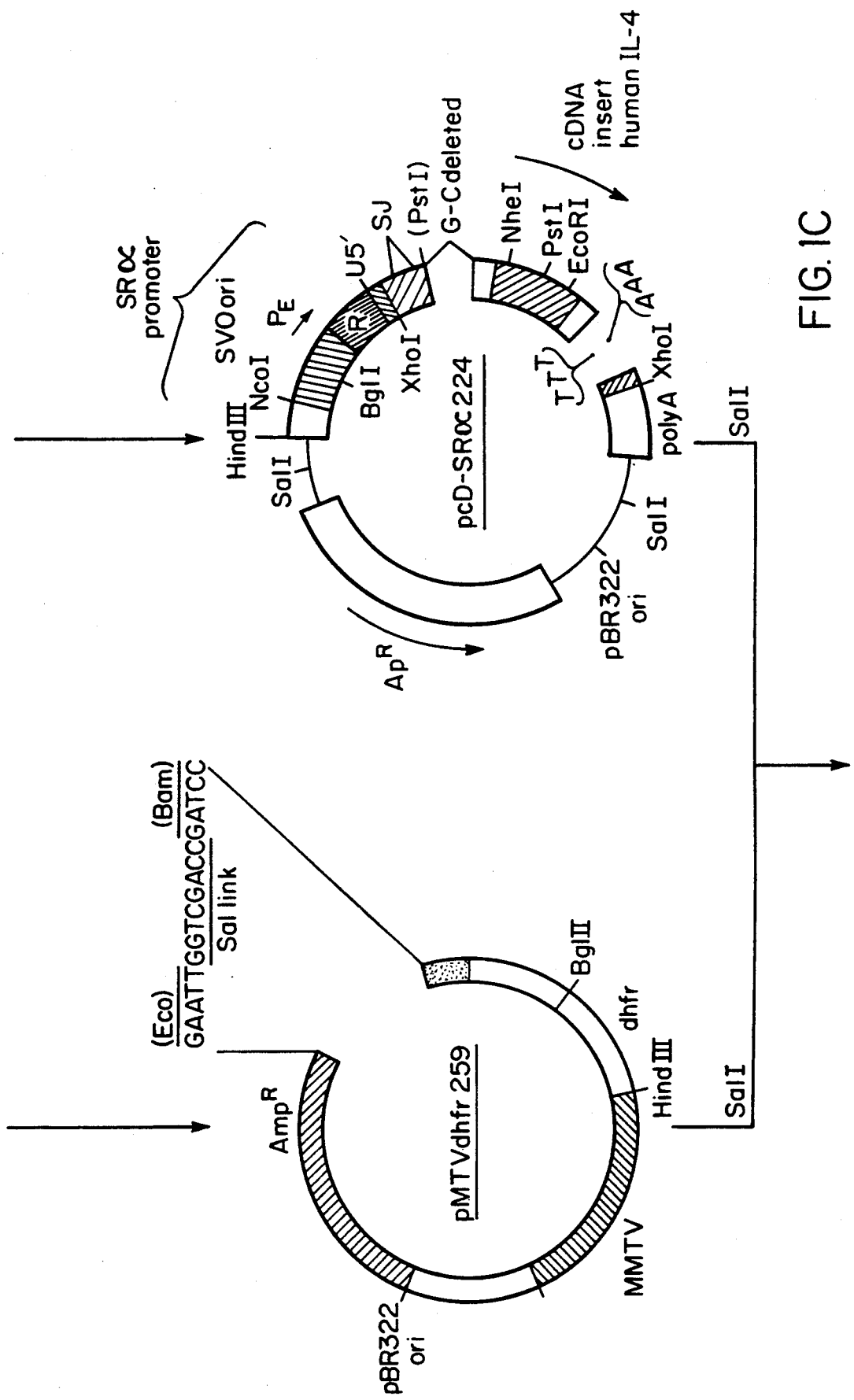
Figure 1D:
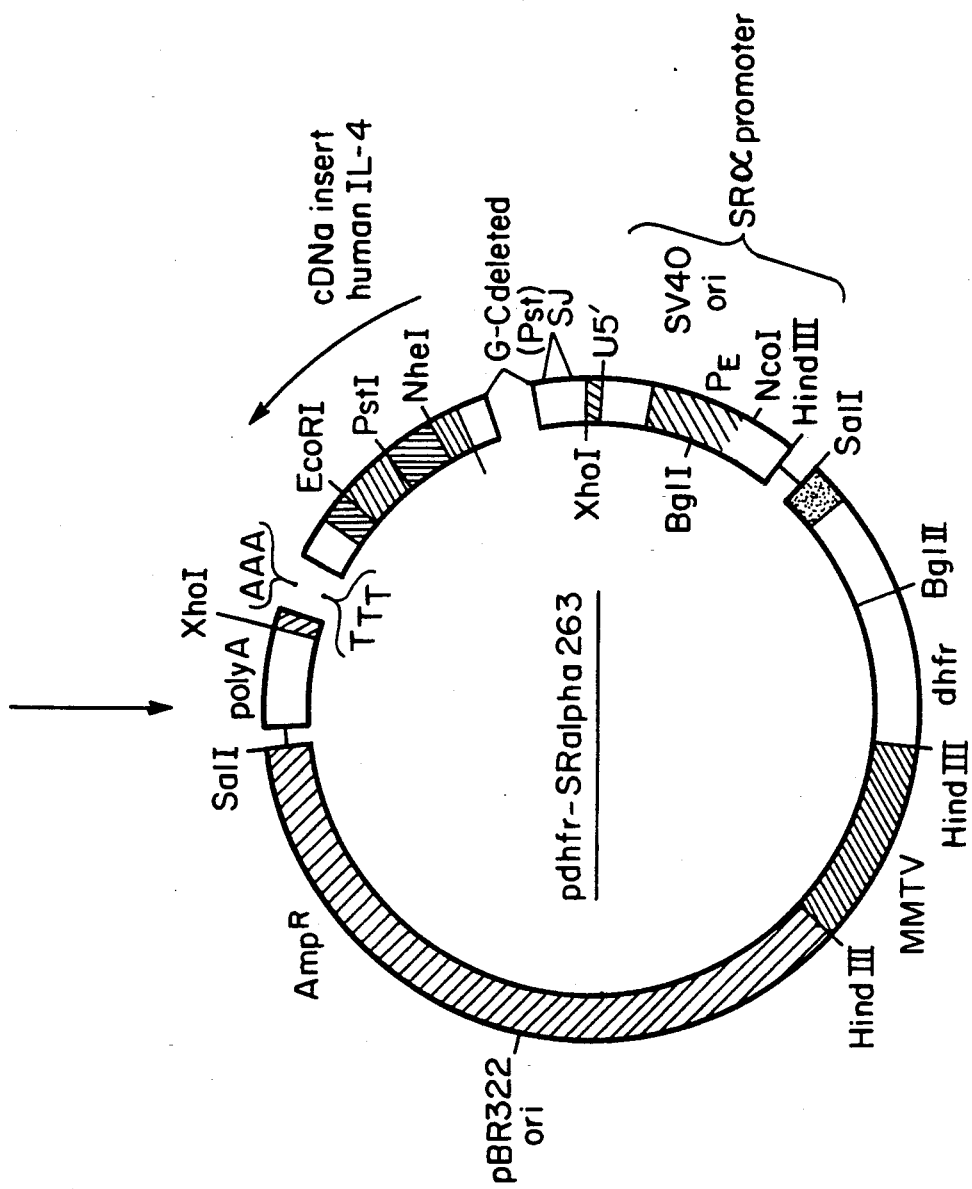

A SalI site was introduced into pMTVdhfr (Lee et al., Nature, 294: 228-232 (1981)) by EcoRI/BamHI restriction, Klenow polymerase fill in of the overhang and ligation to an octanucleotide SalI linker as shown in FIG. 1c. Plasmid pMTVdhfr259, then, lacks restriction sites for EcoRI and BamHI and the region between the two is replaced with a SalI linker. The SalI fragment of pcD-SRa224 containing the Sra promoter, SV40 SJ, human IL 4 cDNA and SV40 polyadenylation signals was inserted into the unique SalI site of pMTVdhfr259 as shown in FIG. 1d. The final human IL-4 expression plasmid, pdhfr-SRalpha263 contains the following elements, counterclockwise from the SalI site:

1. Ampicillin resistance gene and origin of replication from pBR322.
2. MMTV LTR driven dhfr expression unit from pMTVdhfr.
3. SRalpha promoter.
4. SV40 derived splice junction.
5. Human IL-4 cDNA.
6. SV40 derived polyadenylation signal.

The human IL-4 cDNA sequence present in the vector is the same as in pcD-HIL-4 clone 46 given in Yokoto et al., *Proc. Natl. Acad. Sci. USA*, 83: 5894-5895(1986).

DHFR Gene Amplification and Selection of IL-4 SI Line

Chinese hamster ovary cell mutants deficient in dihydrofolate reductase activity (CHO-dhfr) are widely used for overproduction of various recombinant proteins. (Kaufman et al., *Molecular and Cellular Biology*, 5: 1750-1759 (1985)). CHO-dhfr mutant cells have an auxotrophic requirement for hypoxhantine, thymidine and glycine. Expression vectors incorporating a dhfr marker may be used to complement this mutation; selection is achieved by growing cells in the absence of the required media cofactors described above. Gene amplification (increase in copy number up to 1000X) may be accomplished by growing cells in increasing concentration of the folate analog methotrexate (MXT). The amplification of the ingrated recombinant dhfr locus in the genome results in a concomitant increase in copy number of the expression unit for the gene of interest (Ringhold et al., *J. Mol. Applied Genetics*, 1: 165-175 (1081); and Kaufman et al., EMBO J., 6: 187-193 (1987)).

The plasmid DNA having the coding sequence for dhfr and human IL-4 (pdhfr-SRa263) was constructed as described above. Transfection of pdhfr-SRa263 into DXB-II CHO-dhgr cell line was carried out by the calcium phosphate precipitation method. (Graham and Van der Eb, *Virology*, 52: 546 (1978)) Transformants were selected in a selection medium (DMEM, Dulbecco's Modified Eagle's Medium) that lacks hypoxhantine and thymidine. A clone designated 3B12 was chosen for the first cycle of amplification. The 3B12 clone was cultured in a-MEM medium (Eagle's minimum essential medium) containing 40 nM MTX until resistant clones were selected. A clone designated 3B12-A26 was used for further amplification with 1 mm MTX. After the second cycle of drug selection, a clone designated 3B12-A26-19 was chosen for further development. This clone was adapted to growth in a suspension mode with 10% NU Serum TM V and a subclone designated IL-4 SI was selected for the large scale propagation.

Culture Preparation

In order to prepare a Master Cell Bank (MCB), two original 100 ml spinner flasks containing the IL-4 SI cells were used. The cells were carried through two additional growth medium exchanges and grown in 100 ml spinner flasks (growth medium is basal medium plus 0 to 10% serum, e.g., NU Serum TM V). Cells from each flask were collected, washed, resuspended in 10 ml of freezing medium, pooled and aseptically dispensed in about 2.0 ml sterile cell storage vials (freezing medium is basal medium plus 20% serum, e.g., NU Serum TM V plus 10% dimethylsulfoxide). The vials were slowly frozen at $-70\infty$ C. and stored in liquid nitrogen.

The cells from three frozen vials were thawed and propagated by suspension in growth medium for 4 to 6 generations in spinner flasks of increasing volume from 100 ml up to 3 liters. Cells were collected by centrifugation, washed, and resuspended in freezing medium. The cell suspension was aseptically dispensed in about 2.0 ml sterile cell storage vials. The vials were slowly frozen at $-70\infty$ C. and stored in liquid nitrogen to constitute the Master Cell Bank (MCB).

A Master Working Cell Bank (MWCB) was prepared from the MCB by thawing 1 to 3 vials of the MCB and propagating the cells in T-flasks and in suspension for 4 to 6 generations in increasing volumes up to 3 liters. Cells were collected, washed, resuspended in freezing medium and aliquoted and frozen as described for the MCB. The MWCB was stored in liquid nitrogen as well.

IL-4 production was carried out in bioreactors of 50 to 200 liters in volume. To start production, one frozen vial from the MWCB was thawed and inoculated into a T-75 flask. From incubation until cell concentration reaches 100% confluency, cells were trypsinized and inoculated into two T-75 flasks (optionally, a T-160 flask can be used). These flasks were again incubated until 100% confluency and the trypsinized cells were used to inoculate a 100 ml spinner flask.

The 100 ml spinner flask was incubated until adequate cell growth was obtained and was used as inoculum for a 250 ml spinner flask. A similar step was repeated in a 1 liter and a 3 liter flask and a 10 to 20 liter bioreactor. Cells from the 10 to 20 liter reactor were used as inoculum for a 50 to 100 liter reactor. This reactor is initially grown batchwise and upon achieving adequate cell concentration, a continuous media perfusion was initiated.

The media used for growth and continuous perfusion was modified Iscove's mdeium, which may be supplemented with up to 10% (e.g., NU Serum TM V). No methoxtrexate was used throughout the production process.

The fermentation stages were carried out under sterile conditions and in closed systems. The key fermentation parameters such as temperature, pH, agitation and aeration were monitored and controlled as appropriate throughout the growth and continuous perfusion stages. Aseptic samples were taken periodically to measure pH, cell density and to check for sterility (absence of bacteria and fungi).

Upon collection of an adequate volume of conditioned media (perfusate), the broth was filtered to remove any cells that may be present, and concentrated via ultrafiltration. The concentrate, which contains crude CHO IL-4, was forwarded to the final purification stages.

Purification of IL-4 from the crude CHO IL-4 concentrate was carried out by performing a cation exchange chromatography on a sulphonate column (e.g., s-Sepharose). This step was typically repeated. Selected pooled fractions from the sulphonate column were then forwarded to a chelate chromatography step (e.g., cobalt-chelate Sepharose). The selected pooled chelate fractions were then diafiltered and concentrated via membrane filtration. The concentration was chromatographed in a gel filtration column (e.g., HR S-200). The pooled fractions which constitute the purified bulk IL-4 were then filtered and stored at $-20\infty$ C. or lower.

The bulk IL-4 was then prepared for injection by thawing and diluted with sterilized water and/or 10 mm citrate buffer.

The above references are hereby incorporated by reference for their relevant teachings of materials and methods used in the construction of the CHO expression system for hIL-4.

TABLE 1

| | Cholesterol Lowering Effect of IL-4 in Monkeys | | | |
|---|---|---|---|---|
| IL-4 Dose | | Week of Dosing[a] | | |
| Animal No. | (mg/kg/day) | −2 | −1 | 3 | 4 |
| 2(M) | 0.0 | 113 | 112 | 116 | 104 |
| 3(M) | 0.0 | 139 | 136 | 133 | 128 |
| 26(M) | 0.0 | 138 | 133 | 140 | 127 |
| 4(F) | 0.0 | 108 | 109 | 116 | 106 |
| 6(F) | 0.0 | 141 | 155 | 136 | 134 |
| 28(F) | 0.0 | 122 | 141 | 160 | 129 |
| 7(M) | 0.025 | 145 | 167 | 117 | 122 |
| 8(M) | 0.025 | 156 | 130 | 130 | 128 |
| 9(M) | 0.025 | 148 | 129 | 131 | 116 |
| 10(M) | 0.025 | 155 | 159 | 134 | 121 |
| 11(M) | 0.025 | 120 | 116 | 96 | 82 |
| 12(M) | 0.025 | 165 | 162 | 123 | 109 |
| 13(M) | 0.125 | 162 | 133 | 110 | 106 |
| 14(M) | 0.125 | 119 | 126 | 99 | 75 |
| 15(M) | 0.125 | 128 | 115 | 72 | 148 |
| 17(F) | 0.125 | 151 | 145 | 106 | 81 |
| 18(F) | 0.125 | 156 | 128 | 90 | 94 |
| 29(F) | 0.125 | 116 | 115 | 87 | 79 |
| 19(M) | 0.600 | 155 | 144 | 89 | ND |
| 21(M) | 0.600 | 190 | 171 | 58 | ND |
| 27(M) | 0.600 | 170 | 171 | ND | ND |
| 22(F) | 0.600 | 119 | 113 | 54[b] | ND |
| 23(F) | 0.600 | 166 | 169 | 65[b] | ND |
| 30(F) | 0.600 | 114 | 110 | 74 | ND |

M = males
F = females
ND = not determined
[a] cholesterol amounts expressed as milligrams per deciliter
[b] measurements taken at 2 weeks after dosing

I claim:

1. A method of treatment for lowering the blood serum cholesterol level in a mammal comprising administering to said mammal a serum cholesterol lowering effective amount of IL-4.

2. The method of treatment of claim 1 wherein said mammal is a human.

3. The method of treatment of claim 1 wherein said IL-4 is human IL-4.

4. The method of treatment claim 1, wherein said IL-4 is administered in an amount of about 0.5 micrograms to about 600 micrograms per kilogram of body weight per dose.

5. The method of treatment of claim 4 wherein said dose is administered daily.

6. The method of treatment as claimed in claim 1, wherein the mode of administration is selected from intravenous infusion or intravenous injection.

7. The method of treatment of claim 4 wherein said IL-4 is administered in an amount of about 0.5 micrograms to about 125 micrograms per kilogram of body weight per dose.

8. The method of treatment of claim 7 wherein said IL-4 is administered in an amount of about 0.5 micrograms to about 30 micrograms per kilogram of body weight per dose.

9. The method of treatment of claim 7 wherein said dose is administered daily.

10. The method of treatment of claim 8 wherein said dose is administered daily.

* * * * *